(12) United States Patent
Marlinghaus et al.

(10) Patent No.: US 10,143,483 B2
(45) Date of Patent: Dec. 4, 2018

(54) DEVICE AND METHOD FOR SHOCK WAVE TREATMENT OF THE HUMAN BRAIN

(71) Applicant: Storz Medical AG, Tägerwilen (CH)

(72) Inventors: Ernst Marlinghaus, Bottighofen (CH); Gerold Heine, Tägerwilen (CH)

(73) Assignee: STORZ MEDICAL AG, Tagerwilen (CH)

( * ) Notice: Subject to any disclaimer, the term of this patent is extended or adjusted under 35 U.S.C. 154(b) by 560 days.

(21) Appl. No.: 14/057,295

(22) Filed: Oct. 18, 2013

(65) Prior Publication Data

US 2014/0114326 A1   Apr. 24, 2014

(30) Foreign Application Priority Data

Oct. 18, 2012   (EP) .................................... 12189007

(51) Int. Cl.
*A61N 7/00* (2006.01)
*A61B 17/225* (2006.01)
(Continued)

(52) U.S. Cl.
CPC ...... *A61B 17/2258* (2013.01); *A61B 17/2256* (2013.01); *A61N 7/02* (2013.01); *A61B 2034/2051* (2016.02); *A61B 2034/2055* (2016.02); *A61B 2034/2063* (2016.02); *A61B 2034/2074* (2016.02);
(Continued)

(58) Field of Classification Search
CPC ............ A61B 17/2256; A61B 17/2258; A61B 2034/2051; A61B 2034/2055; A61B 2034/2063; A61B 2034/2074; A61B 2034/252; A61B 2090/3937; A61B 2090/3945; A61B 2007/0026; A61N 7/02
See application file for complete search history.

(56) References Cited

U.S. PATENT DOCUMENTS 4,736,751 A * 4/1988 Gevins ................. A61B 5/0017
                                                     600/544
5,173,609 A * 12/1992 Lacoste ................... G01T 1/026
                                                     250/370.07
(Continued)

FOREIGN PATENT DOCUMENTS

EP          2494925 A1    9/2012
WO     WO 1997/010758    3/1997
WO     WO 2008/068717    6/2008

OTHER PUBLICATIONS

Office Action in European Patent Application No. 12189007.3 dated Oct. 25, 2013.
(Continued)

*Primary Examiner* — Ruth S Smith
(74) *Attorney, Agent, or Firm* — Yakov S. Sidorin; Quarles & Brady LLP

(57) ABSTRACT

A device for treating the human or animal brain with shockwaves has a shockwave transducer coupled to a position sensor for detecting the position of the shockwave transducer. The device is adapted to evaluate the signals of the position sensor to calculate the position of the focus spot of the shockwave transducer. Furthermore, a mapping device is provided for mapping the movement of the focus spot over a plurality of positions together with the applied shockwave dose at each of the positions. The applied shockwave dose may be indicated on a color display.

17 Claims, 3 Drawing Sheets

(51) Int. Cl.
*A61N 7/02* (2006.01)
*A61B 34/20* (2016.01)
*A61B 90/00* (2016.01)
*A61B 34/00* (2016.01)

(52) U.S. Cl.
CPC . *A61B 2034/252* (2016.02); *A61B 2090/3937* (2016.02); *A61B 2090/3945* (2016.02); *A61N 2007/0026* (2013.01)

(56) References Cited

U.S. PATENT DOCUMENTS

| | | | |
|---|---|---|---|
| 2004/0122323 A1 | 6/2004 | Vortman | 600/439 |
| 2005/0020917 A1* | 1/2005 | Scherch | A61B 8/08 600/437 |
| 2005/0020945 A1 | 1/2005 | Tosaya | 601/2 |
| 2006/0036195 A1* | 2/2006 | Schultheiss | A61H 23/008 601/2 |
| 2007/0239080 A1* | 10/2007 | Schaden | A61H 23/008 601/4 |
| 2010/0286518 A1 | 11/2010 | Lee | 600/439 |
| 2011/0077559 A1 | 3/2011 | Quistgaard | 601/2 |
| 2013/0178693 A1* | 7/2013 | Neuvonen | A61B 5/0042 600/13 |
| 2014/0200489 A1* | 7/2014 | Behar | A61N 7/02 601/3 |
| 2014/0213904 A1* | 7/2014 | Chen | A61N 5/1049 600/439 |

OTHER PUBLICATIONS

Extended European Search Report in European Patent Application No. 12189007.3 dated Mar. 22, 2013.

* cited by examiner

DEVICE AND METHOD FOR SHOCK WAVE TREATMENT OF THE HUMAN BRAIN

PRIORITY CLAIM

This application claims priority to pending European Application No. 12189007.3 filed on Oct. 18, 2012.

BACKGROUND OF THE INVENTION

1. Field of the Invention

The invention relates to a device for Shock Wave Treatment of the human or animal body and preferably the human brain.

2. Description of Relevant Art

Focused shockwaves may be used for treatment of the human or animal body. They are known to have a therapeutic effect on soft tissue and nerves and may be used for treatment of functional disorders as Alzheimer or Parkinson disease and for thrombolysis. The international patent application publication WO 1997/010758 discloses a device for generating shockwaves for the treatment of body tissue and for crushing calculi. To achieve a certain therapeutic effect, the location and the dose of the shockwaves must be controlled. To improve localization of the treated region, the European patent application EP 2 078 503 A1 discloses to use a locating probe being inserted into the human body, which can be located by a magnetic locating system. Such a locating probe may be introduced into hollow organs or bones, but they are not applicable to the human brain. When applying shockwaves to a single, well-defined spot of the human body, controlling the dose may be simply done by controlling the pulse energy and the number of pulses applied. For treatment of the human brain, a larger area or volume must be treated by shockwaves. This cannot be monitored by using such a locating probe, as the probe cannot be introduced into the brain and the probe is only suitable for applying the shockwaves to a small spot having the size of the focus spot of the shockwave transducer. When applying shockwaves to the brain, these must penetrate the cranium, which attenuates the shockwaves. As the thickness of the cranium is not constant, it is not possible to calculate the applied shockwave dose. US 2010/286518 A1 discloses an ultrasound system and method to deliver therapy based on user-defined treatment spaces. US 2011/0077559 A1 discloses an ultrasound therapy head with movement control to control the movement within two axes. US 2004/0122323 discloses a tissue aberration correction in ultrasound therapy. EP 2 494 925 A1 discloses a method and an apparatus for calculating the speed of ultrasound in at least two tissue types. US 2005/0020945 A1 discloses an acoustically-aided cerebrospinal-fluid manipulation for neurodegenerative disease therapy.

SUMMARY OF THE INVENTION

The embodiments are based on the object of providing a device for treating the human or animal brain with shockwaves by means of a shockwave transducer, which allows to apply a predetermined dose into a treated area and/or volume of the brain tissue, which is significantly larger than the size of the focus spot of the shockwave transducer. A further aspect is an automated treatment of a larger surface and/or volume of brain tissue.

In an embodiment, at least one shockwave transducer is provided for generating acoustic energy in the form of shock- or pressure-waves. Generally, the term of shockwaves is used herein for any shock- or pressure-waves. At least one means for detecting the position of the shockwave transducer, herein referred to as a position sensor, is provided. Furthermore, at least one means for evaluating the signals of the at least one position sensor and calculating the position of the focus spot of the at least one shockwave transducer is provided, which herein is referred to as an evaluation means. Preferably, also the size of the focus spot (focal area) of the shockwave transducer is calculated. In most cases, the focus spot has an ellipsoidal shape, which may vary dependent on various parameters, like frequency or tissue. Mapping of the movement of the at least one shockwave transducer over a plurality of positions together with the applied shockwave dose at each of the positions is done by a mapping device. A series of measurements at human craniums has shown that there is a significant absorption of shockwaves penetrating the cranium, depending of the position of the cranium. Furthermore, the absorption depends on the frequency spectrum used. Specifically at higher frequencies there is a higher absorption compared to lower frequencies. Therefore, the mapping device has to calculate the applied shockwave dose in dependence of the thickness of the cranium through which the shockwaves penetrate.

Herein, the term of dose is used for the shockwave power or energy, depending on the specific kind of treatment. It may be specified in J/cm3 when referring to energy delivered into a specific volume, or in J/mm2 when referring to energy delivered to a specific surface area. The dose may vary by using different pulse durations, pulse energies, pulse repetition rates, pulse counts and treatment times. Preferably, energy of 0.01 to 1 mJ/mm2, most preferably 0.1 to 0.3 mJ/mm2 is applied after correction for absorption. The preferred pulse rate is between 1 and 20, most preferably 3-8 pulses per second. It is important to keep the dose in a certain range. There must be a minimum dose to obtain a therapeutic effect, e.g. for thrombolysis, increased circulation, metabolism, removal of Amyloid beta or stimulation of nerves or brain cells. Exceeding a maximum dose must be prevented under any circumstances, as this may lead to dangerous side effects like hemorrhage.

The at least one position sensor may be a means for detecting and/or indicating the position of the shockwave transducer within the 3-dimensional space or on a 2-dimensional surface like the cranium surface. It may include at least one colored marker, like a colored ball attached to the shockwave transducer, which is monitored by a stereotactic camera system. The at least one marker may also be of reflector type or active LED type. It may also be an infrared, ultrasound-, radio- or x-ray location system. Preferably, it does not only detect the position of the shockwave transducer, but also its orientation to determine the direction of the shockwave path. In an alternative embodiment, the orientation of the shockwave transducer may be calculated by using a model or an actual image of the head, assuming that the shockwave transducer is closely positioned to the cranium. There may also be at least one marker attached to a patient's head. Such a marker may serve as position reference of the head. Furthermore, the position sensor and/or the mapping device may calculate the position of the shockwave transducer relative to the at least one marker fixed to the head. The at least one evaluation means evaluates the signals of the at least one position sensor. It calculates the position of the focus spot. Furthermore, it preferably calculates and/or estimates the size and/or form of the focus spot. The results of the evaluation means are forwarded to a mapping device.

The mapping device preferably is a computer or imaging system. It may evaluate and/or record the shockwave dose dependent on the position and/or orientation of the shockwave transducer. This may be done at a plurality of positions as indicated by the at least one position sensor, whereas the plurality of positions preferably forms an area or volume. The mapping device may further indicate the applied dose preferably on a display like a video screen, for example by using a colored map. Furthermore, a warning may be issued, if the dose exceeds a threshold value. The mapping device may further store the applied dose and/or the position and/or orientation of the shockwave transducer on a storage medium and/or forward the information to another device like a computer. In an alternate embodiment, indication may be done acoustically by varying a tone frequency, a sound level, or giving verbal indications about the dose applied. Generally, indication of the applied dose may either be done two dimensional, e.g. by indicating the treated area or three-dimensional, by indicating the treated volume. In another embodiment, the evaluation means does not only provide information about the applied dose, but indicates which area to be treated next to achieve a predetermined, preferably an even distribution of shockwave dose. This may also be done as described previously, for example by colored indication or by acoustic means, for example by using a speaker or headphones. There may also be an indicator at the shockwave transducer, indicating the applied shockwave dose and/or indicating the suggested direction of move. There may also be a speed indicator, indicating the actual speed of the shockwave transducer over the surface of the cranium, for example at the display or at the shockwave transducer itself. The speed indicator may also give an indication to increase or reduce the speed.

In a preferred embodiment, for indicating the applied dose, a standard model of a human cranium may be used, as the variation of locations of the parts of the brain does not vary largely between the individual humans. Therefore, it is even not necessary to make an X-ray image of the brain, although using a precise three-dimensional image of the brain would allow a more precise dosage. If a precise dosage would be required, such an image may be generated by using a CT scanner or MRI. Based on a model or actual image, a two-or three-dimensional image of the treated area may be made. Furthermore, dose calculations may be made considering the structure and preferably the thickness of the cranium bone structure. In the case of a model, there may be estimates. In the case of an actual image, calculations that are more precise can be made. By using a model or an actual image of the cranium together with the position of the shockwave transducer, preferably combined with the orientation of the shockwave transducer, a comparatively precise calculation of the focus spot may be made. This is much simpler than introducing a sensor into the body as disclosed by prior art. Based on the cranium bone structure, the shockwave energy reaching the tissue below the bone may be calculated. Furthermore an estimate may be made, which dose is required in dependence of the bone above the brain tissue to be treated and/or in the dependence of the specific section of brain. It is furthermore preferred, if the shockwaves dose is reduced or even set to zero in sensitive regions, which may be the area of the auditory ossicle. Although the model and/or image are primarily used by the mapping device, they may also be used by the evaluation means for a better calculation of the position of the focus spot and/or size of the focus spot.

According to a further embodiment, there may be a sensor for measuring the thickness of a bone below the shockwave transducer attached to the shockwave transducer or integrated within the shockwave transducer. Preferably, this sensor is provided at the center of the shockwave transducer. The signals of this sensor may be delivered to the evaluation means and/or mapping device to correct their outputs in dependency of the thickness of the bone.

In a further embodiment, the mapping device may issue a control signal to the signal generator driving the shockwave transducer or to the shockwave transducer itself to modify the dose. The dose may be modified for example by modifying pulse length, pulse energy, pulse rate dependent on the position and/or orientation and/or speed of movement of the shockwave transducer. Preferably, the shockwave dose is controlled in such a way that it meets a predetermined value and preferably is constant over a predetermined region. As an example, if the transducer is moved over an area already treated, the dose would be reduced significantly or even the transducer may be stopped emitting shockwaves. lithe area did not receive the predetermined dose, the transducer may emit the required remaining dose.

In a further embodiment, there may be a means for moving the focus spot of the shockwave transducer and/or the shockwave transducer itself. The focus spot of the shockwave transducer may be modified by adapting the excitation frequency and/or by mechanically moving parts like a reflector of the transducer. This preferably allows modifying the depth of penetration into the tissue. There may be an automatic modification of the focus spot to meet a predetermined depth or dose of shockwaves. To reach a certain volume in depth, there may be a sequence of shockwave pulses with alternating focus points. For example there may be staggering focus depths of 15 mm, 20 mm, 25 mm in three consecutive pulses. By moving the position and/or orientation of the shockwave transducer itself, the place of treatment may be modified. This may be done in accordance with a calculated dose based on a model or an actual image. Here the shockwave transducer may be automatically moved to scan a predetermined area. For the case, the shockwave transducer has a plurality of focus spots, either all focus spots may be mapped by the mapping device or a selection of at least one focus spot is mapped. Herein, preferably the focus spot having the highest intensity is selected.

Generally, the device and the method disclosed herein are not limited to application to brain tissue. Instead, they may be used to any kind of tissue, where a volume or surface area larger than the focus spot of a shockwave transducer has to be treated.

Another embodiment relates to a method of mapping of the shockwave dose applied to a certain area or volume of tissue. This method may include the steps of:
- detecting the position of at least one shockwave transducer,
- calculating the position of the focus spot of the at least one shockwave transducer, and
- mapping the movement of the at least one shockwave transducer over a plurality of positions together with the applied shockwave dose at each of the positions.

The method may further include at least one of the steps of:
- obtaining a model and/or image of at least one of the head, the cranium, the brain,
- calculating and/or indicating the required and/or applied dose,
- controlling the shockwave transducer to emit a dose according to a required and/or calculated dose distribution.

A further embodiment relates to a method of treatment of the human or animal body by using shockwaves. The preferred energy and pulse rate is as mentioned above. According to the method, shockwaves are emitted into human or animal tissue as described above, preferably into animal or human brain. The method may include at least one of the steps of placing a shockwave transducer on the head and emitting shockwaves, detecting the position of at least one shockwave transducer, calculating the position of the focus spot of the at least one shockwave transducer, and mapping the movement of the focus spot of the at least one shockwave transducer over a plurality of positions together with the applied shockwave dose at each of the positions.

The further features of the devices disclosed herein may also be included into the methods disclosed herein.

The method may further include at least one of the steps of:

calculating a model and/or image of at least one of the head, the cranium, the brain, obtaining and/or indicating the required and/or applied dose, moving the shockwave transducer based on the calculation and/or indication to obtain a required and/or calculated dose distribution, controlling the shockwave transducer to emit a dose according to a required and/or calculated dose distribution.

BRIEF DESCRIPTION OF THE DRAWINGS

In the following, the invention will be described by way of example, without limitation of the general inventive concept, on examples of embodiment and with reference to the drawings.

Figure 1:
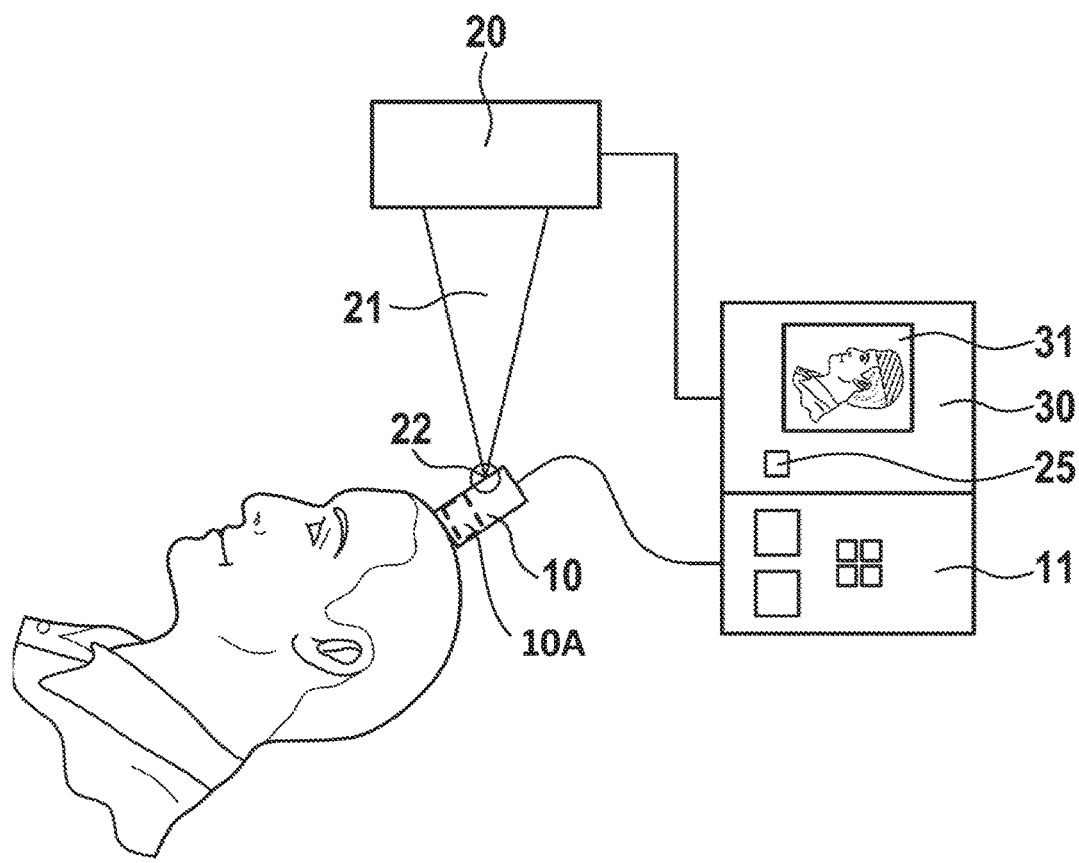
FIG. 1 shows a preferred embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In FIG. 1, a preferred embodiment is shown. A shockwave transducer 10 is applied to the head 80 of a patient. A signal generator 11 delivers the electrical signals and/or power to generate shockwaves by the transducer 10. A position sensor 20 detects the position of the shockwave transducer 10 in 3-dimensional space or on the 2-dimensional surface of the cranium. It may use a beam of light 21 detecting a preferably colored marker 22, which is attached to the shockwave transducer 10. There may be a sensor 10A configured to measure the thickness of a bone below the shockwave transducer 10. From the position and orientation of the marker, which may even, have the color pattern and/or a non-symmetrical shape, the sensor may also derive the orientation of the transducer 10. A mapping device 30 is connected to the position sensor 20 and receives position information thereof The mapping device itself provides means for mapping the movement of the shockwave transducer over a plurality of positions together with the applied shockwave dose at each of the positions. In this embodiment, the mapping device further includes an evaluation means 25 for evaluating the signals of a position sensor 20 and calculating the position of the focus spot of the shockwave transducer 10. In another embodiment, the evaluation means may be separated from the mapping device, although and integration would be economic, as the evaluation function may be implemented by hardware and/or software on a microprocessor or microcomputer which may already be contained in the mapping device 30. To improve mapping, the mapping device may use a standard model of a human cranium, which would be sufficient in most cases. Therefore, x-ray images are no more required. Anyway, x-ray images may still be used for mapping the shockwave dose related to the tissue location. By using this standard model or two x-ray images, the calculation of the focus spot may further be improved in accuracy. This may be done either by the evaluation means or by the mapping device.

Herein, the mapping device 30 is also connected to the signal generator 11 and may receive information about the shockwave dose. Furthermore, it may control the signal output of the signal generator, therefore controlling the shockwaves emitted by shockwave transducer 10. It may modify pulse length, pulse energy, pulse rate dependent on the position and/or orientation and/or speed of movement of the shockwave transducer. There may also be a means for modifying the position of the focus spot of the shockwave transducer to reach a required position within the tissue. The mapping device furthermore may give information, where the shockwave transducer should be moved next. This may be done optically, like using a display 31 or acoustically like by tone with varying amplitude and/or frequency or by spoken information. In an alternative embodiment, there may be a handling device (not shown herein) for moving the shockwave transducer controlled by the mapping device.

Figure 2:
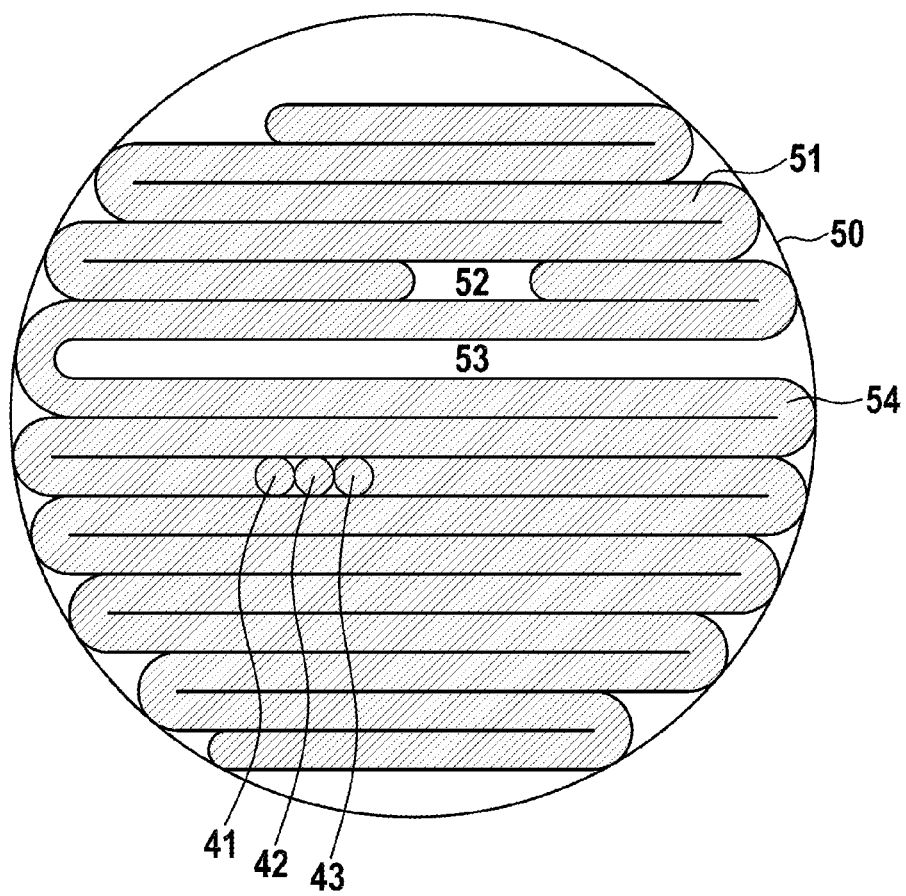
FIG. 2 shows an exemplary area of treatment.

In FIG. 2, an exemplary area of treatment 50 is shown. An image similar as shown in this figure may be drawn on a display to indicate which area has already been treated and which area needs further treatment. In this example, the first track 51 produced by moving the shockwave transducer over the head was interrupted producing a gap 52. After this gap, movement was resumed, resulting in a second track 54. Here region 53 was not treated. This will be indicated, therefore offering the surgeon the opportunity to re-treat this region, if it was not intentionally omitted. Furthermore, in this figure exemplary positions 41, 42 and 43 of the shockwave transducer are shown. The mapping device evaluates, displays and stores the shockwave dose applied to each of such positions resulting in a global dose image. The tracks shown herein consist of a plurality of such adjacent positions. For clarity, only the exemplary positions are shown.

Figure 3:
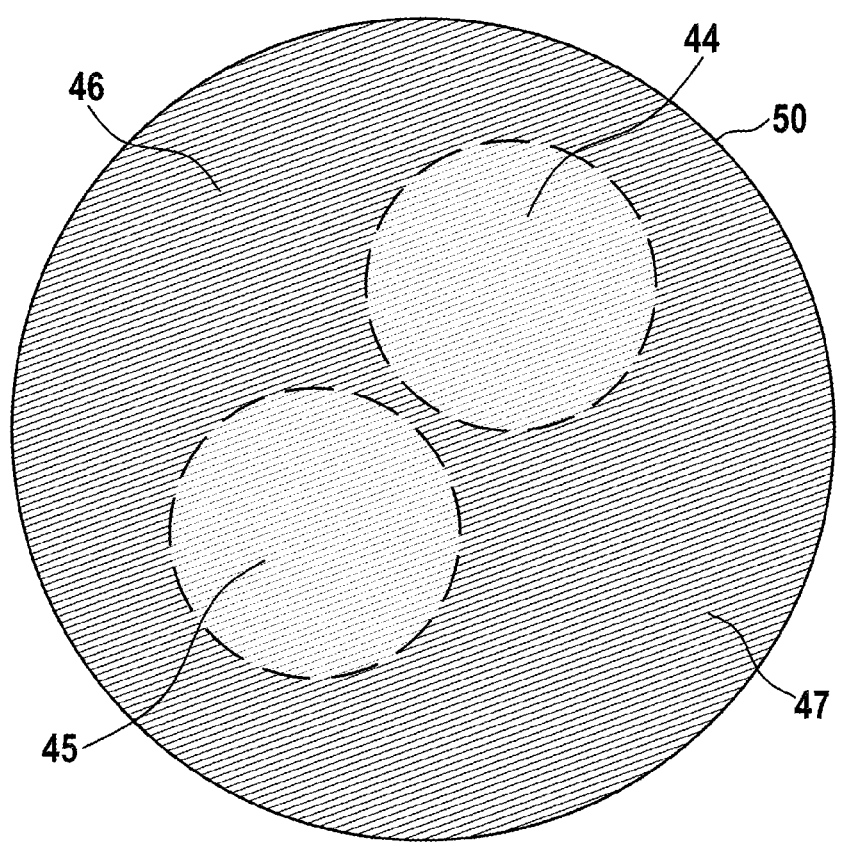
FIG. 3 shows a different display of an area of treatment.

In FIG. 3, a different way of indicating the treatment area is shown. Herein, not the individual tracks as in the picture above are displayed. Instead, the dose of shockwaves is shown, preferably by color shades. In this image, there are areas of lower dose 44, 45, which may be marked by a lighter color and areas of higher dose 46, 47 that may be marked by a darker color. The lighter colors of areas of lower dose 44, 45 may indicate that a further treatment of these areas is required.

It will be appreciated to those skilled in the art having the benefit of this disclosure that this invention is believed to provide a device for Shock Wave Treatment of the human or animal body. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

10A sensor for measuring thickness of a bone

The invention claimed is:

1. A device for treating a human brain through a cranium of the human with shockwaves, comprising
a shockwave transducer,
a position sensor configured to provide at least one signal indicating a position of the shockwave transducer outside the cranium, and
an imaging system
including an evaluation means for evaluating the at least one signal from the position sensor and calculating a position of a focus spot of a shockwave applied by the shockwave transducer inside the cranium, and
configured
1) with the use of at least one of (a) a model of the cranium and (b) an image of the cranium,
to calculate, at a plurality of positions of the focus spot, a first shockwave dose delivered to a tissue of the human brain at each of the plurality of said positions of the focus spot, defined as a result of a movement of the focus spot over the plurality of said positions, due to cranium thinckness and taking into account attenuation caused by the cranium; and
2) to map (i) a movement of the focus spot over a plurality of positions of the focus spot together with (ii) the first shockwave dose calculated to be delivered to a tissue of the human brain at each of the positions of the focus spot.

2. The device for treating the human brain with shockwaves according to claim 1, wherein the plurality of said positions define a treatment area or volume.

3. The device for treating the human brain with shockwaves according to claim 1, wherein the imaging system is configured to calculate said first shockwave dose as a function of a thickness of the cranium.

4. The device for treating the human brain with shockwaves according to claim 1, wherein the imaging system is operably connected to a display configured to indicate the first shockwave dose dependent on the positions.

5. The device for treating the human brain with shockwaves according to claim 1, wherein the imaging system has a three-dimensional display configured to display the model of the cranium.

6. The device for treating the human brain with shockwaves according to claim 1, wherein the imaging system is configured to indicate which areas of the brain have been treated and which areas of the brain still need treatment.

7. The device for treating the human brain with shockwaves according to claim 1, wherein the imaging system is configured to issue a warning, when a predetermined dose is exceeded.

8. The device for treating the human brain with shockwaves according to claim 1, wherein the imaging system is configured to use at least one marker fixed to a head of the human as a position reference.

9. The device for treating the human brain with shockwaves according to claim 8, wherein the imaging system is configured to calculate the position of the shockwave transducer relative to the at least one marker fixed to the head.

10. The device for treating the human brain with shockwaves according to claim 1, wherein the position sensor is further configured to provide at least one signal indicating an orientation of the shockwave transducer outside the cranium.

11. The device for treating the human brain with shockwaves according to claim 1, further comprising a sensor configured to measure a thickness of the cranium at a location corresponding to the position of the shockwave transducer.

12. A method of mapping of a shockwave dose applied through a cranium of a patient to a certain area or volume of tissue within the cranium, comprising the steps of:
detecting a position of a shockwave transducer outside the cranium with a position sensor,
with a programmable computer processor, calculating
a) a plurality of positions of a focus spot of a shockwave formed by the shockwave transducer inside the cranium, and
b) a first shockwave dose reaching the tissue at each of the positions, from the plurality of positions, due to cranium thickness and taking into account attenuation caused by the cranium,
mapping, over the plurality of calculated positions of the focus spot, a movement of the focus spot with a first shockwave dose,
with said processor, calculating, using at least one of (i) a model of at least one of a head, the cranium, and the brain, and (ii) an image of at least one of a head, the cranium, and the brain,
a second shockwave dose, required to be applied to the tissue at each of said positions as a function of a thickness of the cranium.

13. The method according to claim 12, further comprising the step of displaying the image of the at least one of the head, the cranium, and the brain at a display, operably connected to said processor.

14. The method according to claim 12, further comprising at least one step selected from the group of steps consisting of:
on a display, operably connected to said processor,
indicating, as a function of a position at said tissue, the second shockwave dose, and
displaying, as a function of a position at said tissue, the first shockwave dose.

15. The method according to claim 14, wherein said displaying includes forming a visually-perceived map having areas that are color-shaded according to values of the first shockwave dose corresponding to said areas.

16. The method according to claim 12, further comprising at least one step selected from the group of steps consisting of:

controlling the shockwave transducer to emit a dose according to the second shockwave dose required to be applied to the tissue as a function of a thickness of the cranium, and controlling the shockwave transducer to emit a dose according to a desired distribution of the first shockwave dose.

17. The method according to claim 12, further comprising refocusing the shockwave transducer by changing an excitation frequency of said shockwave to form said focus spot at different depths at the tissue.

* * * * *